United States Patent [19]

Sato et al.

[11] Patent Number: 4,898,890
[45] Date of Patent: Feb. 6, 1990

[54] MEDICINES FOR USE IN THE THERAPY AND PREVENTION OF KIDNEY AND LIVER DISEASES

[75] Inventors: Toshio Sato; Hitoshi Matsumoto; Hisao Kakegawa, all of Tokushima, Japan

[73] Assignees: Dainippon Ink and Chemicals, Inc.; Nippon Hypox Laboratories Incorporated, both of Tokyo, Japan

[21] Appl. No.: 157,509

[22] PCT Filed: Jun. 22, 1987

[86] PCT No.: PCT/JP87/00409

§ 371 Date: Dec. 23, 1987

§ 102(e) Date: Dec. 23, 1987

[87] PCT Pub. No.: WO87/07835

PCT Pub. Date: Dec. 30, 1987

[30] Foreign Application Priority Data

Jun. 21, 1986 [JP] Japan ................... 61-145829
Sep. 2, 1986 [JP] Japan ................... 61-205118

[51] Int. Cl.$^4$ ............................ C07O 311/60
[52] U.S. Cl. ..................... 514/685; 514/687; 514/734; 514/885
[58] Field of Search ............ 514/685, 687, 734, 885, 514/886, 893, 926

[56] References Cited

U.S. PATENT DOCUMENTS

| | | | |
|---|---|---|---|
| 3,558,612 | 1/1971 | Kuhn et al. | |
| 3,928,421 | 12/1975 | Kyogoku et al. | 514/927 |
| 4,163,859 | 8/1979 | Sprenger . | |
| 4,279,930 | 7/1981 | Hall et al. | 514/685 |
| 4,510,159 | 4/1985 | Albert et al. | 514/893 |
| 4,537,903 | 8/1985 | Chang et al. | 514/456 |
| 4,540,697 | 9/1985 | Frenke et al. | |
| 4,644,011 | 2/1987 | Baileneger et al. | 514/316 |
| 4,661,499 | 4/1987 | Young et al. | 514/311 |
| 4,663,347 | 5/1987 | Atkinson et al. | 514/467 |
| 4,666,907 | 5/1987 | Fortin et al. | 514/226.2 |
| 4,666,928 | 5/1987 | Young et al. | 514/350 |

FOREIGN PATENT DOCUMENTS

| | | |
|---|---|---|
| 108986 | 5/1984 | European Pat. Off. . |
| 118571 | 9/1984 | European Pat. Off. . |
| 170105 | 2/1986 | European Pat. Off. . |
| 210772 | 2/1987 | European Pat. Off. . |
| 60-178815 | 9/1985 | Japan . |
| 62-185037 | 8/1987 | Japan . |

OTHER PUBLICATIONS

Lawrence et al., Chen Ab. #87:177361 (1977), Analogs of Anthracene, Phenantrene, and Benzoflavone inhibit Prostaglandin Biosynthesis by Cells in Culture.
Oganesvan, et al., Chem Abs. #105:126832 (1986), "Study of Structure–Activity Interrelations in the Flavoid Series.
Chemical Abstracts, vol. 102, No. 23, Abstract No. 199302c (Chem. Abstr. 102:199302c) 10 Jun. 1985 (10.06.85) (Columbus, Ohio, U.S.A.), Nakadate T. et al., Ensho, 4 (4), 554.
Chemical Abstracts, vol. 102, No. 7, Abstract No. 55766j (Chem. Abstr. 102:55766j) 18 Feb. 1985 (18.02.85) (Columbus, Ohio, USA), Takahashi S., et al., Kanko Shikiso 89, 1.
Chemical Abstracts, vol. 103, No. 17, Abstract No. 136542f (Chem. Abstr. 103:136542f) 28 Oct. 1985 (28.10.85) (Columbus, Ohio, USA), Friedman F. K. et al., Pharmacology, 31 (4), 203.
Toshio Satoh et al., Fifth Medicinal Chemistry Symposium Preliminary Publication, p. 68 (1983).
"Prostaglandin System and Inflammation", G. P. Volo, M. E. Fracasso, R. Leone & R. Milanino–*The Prostaglandin System*–Plenum Press, pp. 97–108.
Roderick J. Flower *Pharmacological Reviews*, vol. 26, No. 1, pp 33–61 (1974), "Drugs which Inhibit Prostaglandin Biosynthesis".
Ensho–vol. 4, Autumn, pp. 554–556 (1984), 1 Original Japanese and 1 English translation.
*Toxicologic Pathology*, vol. 14, No. 1, pp. 83–90 (1986), "Renal Toxicity of Non-Steriodal Anti-Inflammatory Drugs", Hugh E. Black.
*Tips*, May (1984), pp. 205–208, "Side Effects of Nonsteroidal Anti–Inflammatory Drugs:Renal, Hepatic and Other Systems", Kim Rainsford.
*Clinical Pharmacy*, vol. 3, Mar.–Apr. (1984), pp. 128–138, "Hepatic Toxicity of Nonsteroidal Anti-Inflammatory Drugs", James H. Lewis.
*Drug Intell. & Clin. Pharm.*, vol. 21, Dec. (1987), pp 954–960, "Nonsteroidal Antiinflammatory Drug–Induced Renal Dysfunction Related ... ", R. G. D'Angio.
*AM. J. Nephrol.*, vol. 7, pp. 408–418 (1987), "Renal Physiology of the Prostaglandins and the Effects of Nonsteriodal Anti–Inflammatory Agents", Hart et al.
*Khim.–Farm. ZH.* (1986), vol. 20, No. 6, pp. 696–702, "Study of Structure–Activity(SA) Interrelations in the Flavonoid Series." Oganesvan et al.
"Iyakuhin Youran (The Survey of Ethical Drugs)", 4th Edition, Pub. 31 Mar. 1988, Yakugyo Jiho Co., Ltd., pp. 1382–1384.
"Ihou–Syukai", pp. 128, 187–188, 304–305, 311, & 366–368, Bunkou–Tosyo Co., Ltd. (Chinese).
*Ency. Of Common Natural Ingredients used in Food*, (List continued on next page.)

Primary Examiner—H. M. S. Sneed
Assistant Examiner—J. Saba
Attorney, Agent, or Firm—Oblon, Spivak, McClelland, Maier & Neustadt

[57] ABSTRACT

A novel medicine containing isoliquiritigenin as the active ingredient is disclosed, which exhibits excellent effects when used as a medicine for the therapy and prevention of kidney diseases, a medicine for the therapy and prevention of liver diseases, and a medicine for the therapy and prevention of complication resulting from diseases of these organs.

52 Claims, No Drawings

OTHER PUBLICATIONS

*Drugs and Cosmetics* (1980), Albert V. Leung, pp. 220–222, Wiley-Interscience.

Planta Medica, vol. 50, No. 4, Aug. 1984, pp. 298–302 * p. 301, right-hand column, lines 5–13.

Journal of Traditional Chinese Medicine, vol. 4, No. 2, 1984, pp. 127–132; S. Xianshi et al: "Clinical and Laboratory observation on the Effect of Glycyrrhizin in Acute and Chronic Viral Hepatitis" * p. 132, left-hand column, lines 1–14, 31–41.

Chemical Abstracts, vol. 84, No. 8, 23 Feb. 1976, p. 400, Abstract No. 49837k, Columbus, OH, U.S.: G. Proske: "Assay of succus liquiritiae in drugs. Analysis of Bisuc", and Arch. Pharm. (Weinheim, Ger.) 1975, 308(11), 832–9.

Chemical Abstracts, vol. 102, No. 9, 4 Mar. 1985, p. 322, Abstract No. 75705s, Columbus, OH, U.S.: D. Zhu et al: "Chemical Constituents of Glycyrrhiza Uralensis Fisch-Structures of Isolicoflavonol and Glycycoumarin", Xuchao, 1984, 42(10), & Huaxue 1080–4.

File WPIL, No. 88–165728, Derwent Publications Ltd., London, GB; and JP-A-63 104 920 (Tsumura Juntendo K.K.) 10–05–88.

MEDICINES FOR USE IN THE THERAPY AND PREVENTION OF KIDNEY AND LIVER DISEASES

TECHNICAL FIELD

The present invention relates to medicines for use in the therapy and prevention of kidney and liver diseases, and more particularly to medicines of this kind which can exhibit excellent therapeutic and preventive effects with respect to kidney or liver diseases individually developed or to complications resulting from diseases of these organs.

BACKGROUND ART

As is well known, the kidney in a vital organism performs at its renal tubule and with its filtration and secretion mechanism the function of excreting into the urine waste substances from blood and noxious substances taken up by the vital organism, such as drugs and toxic substances.

On the other hand, the liver in a vital organism performs three major functions, as listed below. Namely, the liver first acts as a digestive gland and secretes 500 to 1000 cc of bile per day to assist in the digestion and absorption of fats by the small intestines. Its second function is to process chemical changes, storage, and use of various nutrients within the body; in brief, it is an intermediate metabolism. Thirdly, the liver performs detoxication by subjecting noxious substances, such as toxin, from outside the body and toxic substances produced within the body, to detoxication treatments such as oxidization, reduction and inclusion, and by mixing these substances with bile to dispose of them or by sending them to the kidney for excretion into the urine.

In this way, although the kidney and the liver perform their individual functions, the above-mentioned waste substances and drugs tend to accumulate locally, and therefore these substances often cause kidney diseases and liver diseases to develop, not only individually but also as complications resulting from diseases of these organs. Specific substances which can cause such individual or complicated kidney and liver diseases are of various types. For instance, drugs which can act as such substances are listed below and are classified according to the organs to be affected. In the following list, the drugs marked with the symbol ⊚ are those which can cause injury to both the kidney and the liver.

Drugs possessing the tendency to cause kidney injury

⊚Analgestics, antipyretics, anti-inflammatory drugs, and antirheumatic drugs:
  phenacetin, aspirin, indomethacin, mefenamic acid, fenprofen, gold compounds, D-penicillamine, etc.
⊚Antibiotics:
  aminoglycosides, polypeptides, polyenes, cephalosporins, penicillines, etc.
⊚Chemotherapeutic drugs:
  sulfamides, etc.
⊚Anti-cancer drugs:
  mitomycin C, daunomycin, cis-platinum, nitrosoureas, etc.
. Immunosuppressants:
  cyclophosphamide, etc.
⊚Anesthetics:
  methoxyflurane, etc.
⊚Diuretics:
  thiazides, etc.
. Contrast media Drugs possessing the tendency to cause liver injury ⊚Analgestics, antipyretics, anti-inflammatory drugs, and antirheumatic drugs:
  acetaminophen, aspirin, phenylbutazone, sulindac, ibufenac, gold compounds, etc.
⊚Antibiotics:
  aminoglycosides, polypeptides, cephalosporins, penicillines, tetracyclines, etc.
⊚Chemotherapeutic agents:
  sulfa drugs, isoniazides, etc.
⊚Anti-cancer drugs:
  mitomycin C, cis-platinum, 6-MP, nitrosoureas, etc.
⊚Anesthetics:
  halothane, methoxyflurane, etc.
. Psychotropic drugs:
  chlorpromazines, diazepams, barbitals, etc.
⊚Diuretics:
  thiazides, etc.

The above-listed examples of drugs which can cause kidney and liver diseases are arranged in order based on the following publications:

RINSHOH SEIJINBYOH (Clinical Studies of Adult Diseases), No.8, vol, 16, (1986), pages 45 to 62 and 85 to 103; SAISHIN IGAKU BUNKO, 42 "Mansei Kan'en no Shinryoh (Diagnosis and Treatment of Chronic Hepatitis)" by Mikio Nishioka, published by Shinkoh Igaku Shuppan-sha K.K. on January 26, 1987, pages 29 to 31; RINSHOH TO KENKYUH (Clinical Studies), No. 4, vol. 63 (published in Apr. 1986), pages 38 to 39; KANZOH NO BYOHKI (Liver Diseases), by Toshitsugu Orita et al, published by Chuhgai Igaku-sha on October 20, 1980, pages 323 to 333; and IYAKUHIN YOHRAN (Handbook of Medical Articles), edited by Osaka-Fu Byohin Yakuzaishi-Kai, published by Yakugyo Jihoh Sha on Nov. 10, 1983.

Hereinabove, kidney and liver diseases have been discussed from the viewpoint of the metabolic functions of these organs. However, some kidney diseases are considered to be caused by the intermediary of the immunological mechanism.

Kidney diseases specified herein are the following: (a) a functional disorder of the kidney which is caused by abnormality in the above-mentioned metabolic functions, including acute hepatitis caused by drugs, etc., and chronic nephritis developed from such acute nephritis; (b) acute nephritis caused by the intermediary of the immunological mechanism and chronic nephritis developed from such acute nephritis; and (c) acute nephritis caused by bacteria and virus infection and chronic nephritis developed from such acute nephritis, including a wide range of functional disorders of kidney sites such as the glomerulus, renal tubule and the lupus.

Similarly, liver diseases specified herein are the following: (a) a functional disorder of the liver which is caused by abnormality in the above-mentioned metabolic functions and in the biosynthetic functions, including acute hepatitis caused by drugs, etc., and chronic hepatitis developed from such acute hepatitis; (b) fatty liver caused by drinking, etc. and chronic hepatitis developed from such fatty liver; and (c) viral hepatitis caused by virus infection and chronic hepatitis developed from such acute hepatitis, including liver cirrhosis as a result of diseases involving a wide range of such functional disorders of the liver.

Known therapeutic methods of treating kidney diseases are adopted in accordance with the seriousness of the disease with a view to maintaining the functions of the liver, and they include rest therapy, dietetic therapy, drug therapy, hemodialysis, and kidney transplantation. Hemodialysis is considered to be the final treatment available for patients suffering from kidney disease. However, this treatment can only remove from the blood waste substances stored within the body due to the functional disorders of the kidney, and cannot improve the kidney function per se. Thus, such patients have to receive hemodialysis throughout their life and, in the end, most of them will suffer from a complication accompanied by cardiac insufficiency, an infectious disease, etc., and may die from such a complication. Some forms of the drug therapy practiced at present use, for example, diuretics, immunosuppressants, and corticoid, while others use mannitol and lactulose. However, these forms are all symptomatic treatments, and their therapeutic effects are not sufficient. Thus, the present situation is that the patients are forced to rely on dietetic therapy and rest therapy. For example, diuretics are used in treating kidney diseases but their pharmacological effects are only to compensate for the lowered functions of the kidney but not to prevent nor cure kidney diseases. In addition, among diuretics, most of the thiazides and furosemide which is a non-thiazide diuretic have side effects which induce functional disorders of the liver and, in this respect, they are not desirable for therapy.

Therefore, with the present situation of drugs available for use in the therapy of kidney diseases, it is apparent that no fully satisfactory drug exists, and the development of a more effective drug is desired.

Similarly, known therapeutic methods of treating liver diseases are methods which are adopted with a view to maintaining the liver functions, and they include rest therapy, dietetic therapy, and drug therapy. Among these types of therapy, specific examples of drug therapy include those using, for instance, amino acid such as aspartic acid, thioctic acid, methionine, thioproline and glycine, and peptides such as glutathione, as well as extract from the liver, hydrolysate from the liver, hydrolysate from the placenta, glucuronic acid derivatives, and glycyrrhizin extracted from Glycyrrhiza and refined. Among these agents, glycyrrhizin is known to be effective for improving the liver functions which have been disordered by chronic hepatitis. However, this agent involves problems in its administration that it is ineffective when orally administered.

Since, the development mechanisms of various liver diseases have not been clarified except those of viral hepatitis and of toxic hepatitis, the methods of treating liver diseases have mainly been rest therapy and dietetic therapy. Recently, however, malotilate has been developed, which suppresses the changing of liver tissues into fibrous tissues by activating the protein synthesis and RNA synthesis. However, the only application of malotilate that is permitted is for the therapy of liver cirrhosis.

Further, cianidanol has been developed as an immunity activating agent although the mechanism of this action is not clarified, and this agent is considered to be effective in the treatment of B-type viral hepatitis. However, because accidents involving the death of patients that were treated with cianidanol have occurred in Italy and Portugal, the sale of cianidanol is prohibited at present in Japan.

Therefore, in the present situation, development of a drug which is truly effective in the therapy and prevention of a wide range of liver diseases, and which is excellent in terms of safety is desired.

Furthermore, as described above, the kidney and the liver play important roles in the metabolism of a vital organism, and are interrelated to each other. This fact means that, when the functions of one of these organs are disordered, the other will have to bear an increased burden in terms of the metabolic functions, often resulting in both organs becoming functionally disordered. Particularly in the case of a patient suffering from a functional disorder of the liver, as the functional disorder proceeds, it will often be accompanied by a functional disorder of the kidney. Therefore, a drug for the therapy which can improve the functions of both organs simultaneously is desired.

DISCLOSURE OF INVENTION

The present inventors have made various studies to solve the problems of the prior art. After examining various types of substances, the present inventors have come to take up isoliquiritigenin and achieved the following findings.

It has been known for long that isoliquiritigenin exists in nature as a component of the plant Glycyrrhiza. However, because the content of the isoliquiritigenin in Glycyrrhiza is small, and moreover the greater part of this component exists in the form of glycosides with a lot of analogous homologus coexisting, the separation and refining of the substance has been difficult, and the question of whether isoliquiritigenin has any pharmacological effects has not hitherto been solved. For instance, Japanese Patent Publication No. 8485/1973 reports that mixtures of liquiritin, isoliquiritin, liquiritigenin, and isoliquiritigenin extracted from Glycyrrhiza have an anti-ulcerous activity. However, the Publication gives no clear report to the effect that isoliquiritigenin, which coexists with other components and is contained in a very small amount, is the active component responsible to the anti-ulcerous activity.

A report (*YAKUGAKU ZASSHI* (Pharmaceutics Journal) vol, 80, pages 620 to 624, 1960) by Shibata et al states that isoliquiritigenin has a relatively strong antispasmodic activity, though the purity of the isoliquiritigenin used is not known.

In recent years, chalcones have attracted attention because of their pharmacological activities. A report (*ENSHOH (INFLAMMATION)*, vol 4, pages 554 to 56, 1984) has been given by Nakadate, et al., concerning the activity of suppressing the rise in permeability of the skin by a carcinogenesis promotor TPA. Japanese Patent Application No. 178815/1985 reports concerning their activity of inducing the differentiation of tumor cells of animals, as well as their usefulness as a carcinostatic substance.

Based on these findings, the present inventors have made their own studies, and previously made a proposal (Japanese Patent Application No. 49530/1986) concerning the use of isoliquiritigenin as an anti-allergic drug. As a result of further studies made on the basis of this finding, the present inventors have newly found that isoliquiritigenin is effective in the therapy and prevention of kidney and liver diseases.

The present invention has been accomplished on the basis of the above-mentioned findings. That is, the present invention provides a medicine for use in the therapy and prevention of kidney and liver diseases, which contains as the active ingredient isoliquiritigenin or pharmaceutically acceptable salts thereof.

As described above, kidney diseases specified herein are the following: (a) a functional disorder of the kidney which is caused by abnormality in the metabolic functions, including acute nephritis caused by drugs, etc., and chronic nephritis developed from such acute nephritis; (b) acute nephritis caused by the intermediary of the immunological mechanism and chronic nephritis developed from such acute nephritis; and (c) acute nephritis caused by bacteria and virus infection and chronic nephritis developed from such acute nephritis, including a wide range of functional disorders at kidney sites such as the glomerulus, renal tubule and the lupus.

Similarly, liver diseases specified herein are the following: (a) a functional disorder of the liver which is caused by abnormality in the metabolic functions and in the biosynthetic functions, including acute hepatitis caused by drugs, etc., and chronic hepatitis developed from such acute hepatitis; (b) fatty liver caused by drinking or the like and chronic hepatitis developed from such acute hepatitis; and (c) viral hepatitis caused by virus infection and chronic hepatitis developed from such acute hepatitis, including liver cirrhosis as a result of diseases involving a wide range of such functional disorders of the liver.

Salts of isoliquiritigenin which are pharmaceutically acceptable include non-toxic salts such as salts of alkali metals and alkaline earth metals, for example, sodium salt, potassium salt, magnesium salt and calcium salt, and non-toxic amine salts such as ammonium salt.

The medicine for use in the therapy and prevention of kidney and liver diseases in accordance with the present invention can be administered either orally or parenterally (such as venous injection, subcutaneous injection or rectal administration, etc.), and can be prepared in a formulation which is suitable for the administration method chosen.

The medicine in accordance with the present invention can be prepared in a formulation such as a tablet, a capsule, a granule, a powder, a fine granule, a pill, a troche, a buccal, a suppository, an ointment, an injection, an emulsion, a suspension, or a syrup, depending on the use.

The preparation can be performed by known methods by using a non-toxic additive or additives that are usually employed in the preparation of a medicine of this kind, such as an excipient, a binder, a disintegrator, a lubricant, a preservative, an antioxidant, an isotonizing agent, a buffer, a coating agent, a corrigent, a solution adjuvant, a base, a dispersing agent, a stabilizer, or a colorant.

Specific examples of non-toxic additives that are usable are listed below.

Examples of suitable excipients are starches and their derivatives (dextrin, carboxymethyl starch, etc.), celluloses and their derivatives (methyl cellulose, hydroxypropylmethyl cellulose, etc.), sugars (lactose, saccharose, glucose, etc.), silicic acid and silicates (natural aluminum silicate, magnesium silicate, magnesium metasilicate aluminate, etc.), carbonates (calcium carbonate, magnesium carbonate, sodium bicarbonate, etc.), aluminum hydroxide-magnesium, synthetic hydrotalcite, polyoxyethylene deviratives, glycerin monostearate, and sorbitan monooleate, etc.

Examples of suitable binders are starches and their derivatives (-starch, dextrin, etc.), celluloses and their derivatives (ethyl cellulose, sodium carboxymethyl cellulose, hydroxypropylmethyl cellulose, etc.), gum arabic, tragacanth, gelatin, sugars (glucose, saccharose), ethanol, polyvinyl alcohol, and polyvinyl pyrrolidone, etc.

Examples of suitable disintegrators are starches and their derivatives (carboxymethyl starch, hydroxypropyl starch, etc.), celluloses and their derivatives (carboxymethyl cellulose, sodium carboxymethyl cellulose, crystalline cellulose, hydroxypropylmethyl cellulose, etc.), carbonates (calcium carbonate, sodium bicarbonate, etc.), tragacanth, gelatin, and agar, etc.

Examples of suitable lubricants are stearic acid, calcium stearate, magnesium stearate, talc, silicic acid and its salts (light anhydrous silicic acid, natural aluminum silicate, etc.), titanium oxide, calcium hydrogenphosphate, dry aluminum hydroxide gel, and Macrogol, etc.

Examples of suitable preservatives are para-hydroxybenzoate esters, sulfites (sodium sulfite, sodium pyrosulfite, etc.), phosphates (sodium phosphate, calcium polyphosphate, sodium polyphosphate, sodium metaphosphate, etc.), alcohols (chlorobutanol, benzyl alcohol, etc.), benzalkonium chloride, benzethonium chloride, phenol, cresol, chlorocresol, dehydroacetic acid, sodium dehydroacetate, glycerin sorbate, and sugars, etc.

Examples of suitable antioxidants are sulfites (sodium sulfite, sodium bisulfite, etc.), rongalit, erithorbic acid, L-ascorbic acid, cysteine, acetylcysteine, thioglycerol, butyl hydroxyanisole, dibutyl hydroxytoluene, propyl gallate, ascorbyl palmitate, dl-α-tocopherol, and nordihydroguaiaretic acid, etc.

Examples of suitable isotonizing agents are sodium chloride, potassium nitrate, sodium nitrate, dextran, glycerin, and glucose, etc.

Suitable examples of buffers are sodium carbonate, hydrochloride, boric acid, and phosphates (sodium phosphates, etc.) etc.

Examples of suitable coating agents are derivatives of celluloses (hydroxypropyl cellulose, cellulose acetate phthalate, hydroxypropylmethyl cellulose phthalate, etc.), shellac, polyvinyl pyrrolidone, polyvinyl pyridines (poly-2-vinylpyridine, poly-2-vinyl-5-ethylpyridine, etc.), polyvinyl acetaldiethylamino acetate, polyvinyl alcohol phthalate, and methacrylatemethacrylic acid copolymer, etc.

Examples of suitable corrigents are sugars (glucose, saccharose, lactose, etc.), sodium saccharin, and sugar alcohols, etc.

Examples of suitable solution adjuvants are ethylenediamine, nicotinamide, sodium saccharin, citric acid, citrates, sodium benzoate, soaps, polyvinyl pyrrolidone, polysorbates, sorbitan fatty acid esters, glycerin, propylene glycol, benzyl alcohol, glycerol 1,3-diethyl ether, and sugar esters, etc.

Examples of suitable bases are fats (lard, etc.), vegetable oils (olive oil, sesame oil, etc.), animal oils, lanolin, vaseline, paraffin, wax, resin, bentonite, glycerin, glycols, higher alcohols (stearyl alcohol, cetanol, etc.), and cellulose derivatives, etc.

Examples of suitable dispersing angents are gum arabic, tragacanth, cellulose derivatives (methyl cellulose, etc.), stearic acid polyoxyls, sorbitan sesquioleate, aluminum monostearate, sodium alginate, polysorbates, and sorbitan fatty acid esters, etc.

Finally, examples of suitable stabilizers are sulfites (sodium bisulfite, etc.), nitrogen, and carbon dioxide, etc.

The content of isoliquilitigenin in the medicine varies depending on the formulation of the medicine. In general, it should preferably be contained at a concentration of 0.1 to 100% by weight.

The dosage of the medicine in accordance with the present invention can be varied within a wide range in accordance with the kind of warm-blooded animal, including human beings, to which it is to be administered, the seriousness of the disease, and the diagnosis of the doctor, but the dosage in terms of the active ingredient ranges, when the medicine is orally administered, in general, from 0.01 to 300 mg, preferably from 0.01 to 50 mg, per kilogram body weight per day, and when the medicine is parenterally administered it ranges from 0.01 to 150 mg, preferably 0.01 to 20 mg, per kilogram body weight per day. However, these dosage ranges can be varied in accordance with the seriousness of the disease and the diagnosis of the doctor. Each of the above-mentioned dosages can be divided into portions so that the dosage is administered one to several times a day.

Certain examples of the present invention will now be described, though the present invention is not limited to these examples.

BEST MODE FOR CARRYING OUT THE INVENTION

Example 1

Toxicity Tests

In this example, tests were conducted to confirm the safety of isoliquiritigenin, which is the active ingredient of the medicine in accordance with the present invention.

Isoliquiritigenin was administered by oral administration or intraperitoneal injection to five 5-week-old male ddy mice. As a result, the minimum lethal dose was found to be not less than 3000 mg/kg (oral administration) or not less than 1000 mg/kg (intraperitoneal injection).

Example 2

Activity against acute kidney injury induced by gentamycin

In this example, gentamycin, which is an antibiotics of the aminoglycoside type and is known to have a very strong effect of inducing functional disorders of the kidney, was selected as a model of inducer for drug-induced acute nephritis, which is one of functional disorders of the kidney caused by abnormality in metabolic functions, and the activity of isoliquiritigenin against the acute nephritis induced by gentamycin was examined, to confirm the efficacy of the medicine of the present invention.

The tests were conducted in accordance with the method reported in NIHON YAKURIGAKUKAI SHI, vol. 84, pages 463 to 469, 1984, by Suzuki et al. That is, Wistar strain male rats (produced by Nihon Charles River K.K., 5 rats in each group), each weighing 160 to 180 g, were subcutaneously injected with 80 mg per kilogram body weight per day of gentamycin once a day through the back for 15 days, thereby inducing injury to the kidneys, and then orally administered with 5 ml per kilogram body weight of a mixture in which 50, 150 or 300 mg per kilogram body weight per day of isoliquiritigenin was suspended in aqueous solutions of 1%-carboxymethyl cellulose (hereinafter abbreviated as 1%-CMC), for 15 continuous days. Meanwhile, rats in a solution control group were administered with gentamycin in the same manner as the isoliquiritigenin administration groups, and orally administered with 5 ml per kilogram body weight of aqueous solutions of 1%-CMC, for 15 continuous days. Samples of the urine were collected using metabolism cages for a period of 24 hours from the day before the initial administration to the next day, and for 24 hours from the day of the last administration to the next day. After the amounts of urine were measured, the urine samples were centrifuged at 3000 rpm for 15 minutes, and the supernatant liquids were examined by measuring the activity of lactate dehydrogenase (LDH) within the urine by using an automatic analyzer (AU-550, a product of Olympus Kohgaku Kohgyoh). The activity of N-acetyl-$\beta$-D-glucosaminidase (NAG) within the urine was also measured, by using an NAG Test Shionogi (a product of Shionogi Seiyaku). After the completion of the collection of the urine samples but before the initial administration, blood samples were collected from the tail veins. At the day after the last administration, blood samples were collected from the aorta abdominalis while the rats were anesthetized with ether, and the rats were victimized by loss of blood. They were subjected to abdominal section and the kidneys were removed. After the blood samples were centrifuged at 3000 rpm for 15 minutes, the serum was examined by measuring the urea nitrogen within the blood (BUN) by using an automatic analyzer. The removed kidneys were each divided into two, and, after being fixed in 10%-buffer formalin, samples dyed with hematoxylineosin stain were prepared and were observed under a microscope. The results are shown in Tables 1 and 2.

TABLE 1

| | Biochemical Parameters of Blood and Urine Samples 15 Days after Induction of Kidney Injury by Gentamycin | | | | | |
|---|---|---|---|---|---|---|
| | Biochemical Parameters of Urine Stored for 24 Hours | | | | Biochemical Parameters of Blood | |
| | NAG (U/day · Urine) | | LDH (U/day · Urine) | | BUN (mg/dl) | |
| Isoliquiritigenin Dosage (mg/kg) | Day before Tests* mean ± SD | 15th Day mean ± SD | Day before Tests* mean ± SD | 15th Day mean ± SD | Day before Tests* mean ± SD | 15th Day mean ± SD |
| 0 | 3.2 ± 1.8 | 59.2 ± 15.1 | 0.13 ± 0.05 | 2.10 ± 0.71 | 21.5 ± 1.0 | 29.6 ± 3.1 |
| 50 | 8.0 ± 2.6 | 37.9 ± 23.6 | 0.11 ± 0.05 | 1.67 ± 0.25 | 23.5 ± 0.8 | 20.6 ± 0.9 |
| 150 | 6.6 ± 3.2 | 23.9 ± 19.3 | 0.21 ± 0.14 | 1.47 ± 0.46 | 21.5 ± 2.6 | 19.7 ± 1.9 |
| 300 | 5.7 ± 1.5 | 25.3 ± 18.4 | 0.16 ± 0.04 | 1.13 ± 0.30 | 20.5 ± 3.7 | 17.7 ± 1.1 |

*Biochemical Data of Each Group before the Start of Tests

TABLE 2

Pathological Views of Rats Suffering from Gentamycin-Induced Kidney Injury

| Views of Tissue | Gentamycin Only (GM) 80 mg/Kg/day | | | | Isoliquiritigenin 50 mg/Kg GM 80 mg/Kg/day | | | | Isoliquiritigenin 150 mg/Kg Gm 80 mg/Kg/day | | | | Isoliquiritigenin 300 mg/Kg GM 80 mg/Kg/day | | | |
|---|---|---|---|---|---|---|---|---|---|---|---|---|---|---|---|---|
| Number of Animals | 5 | | | | 5 | | | | 4 | | | | 5 | | | |
| Grade | − | ± | + | ++ | − | ± | + | ++ | − | ± | + | ++ | − | ± | + | ++ |
| Kidney | | | | | | | | | | | | | | | | |
| Necrosis of Renal Tubule Epithelium Cells | 3 | 0 | 2 | 0 | 2 | 2 | 1 | 0 | 2 | 1 | 1 | 0 | 5 | 0 | 0 | 0 |
| Degeneration of Renal Tubule Epithelium Cells | 0 | 0 | 5 | 0 | 1 | 1 | 3 | 0 | 2 | 1 | 1 | 0 | 1 | 1 | 3 | 0 |
| Regeneration of Renal Tubule Epithelium Cells | 0 | 0 | 2 | 3 | 0 | 2 | 3 | 0 | 0 | 0 | 2 | 2 | 0 | 3 | 2 | 0 |
| Expansion of Renal Tubule | 0 | 0 | 5 | 0 | 0 | 0 | 5 | 0 | 0 | 0 | 4 | 0 | 0 | 1 | 4 | 0 |
| Division of Renal Tubule Epithelium Cells | 1 | 0 | 3 | 1 | 2 | 3 | 0 | 0 | 0 | 2 | 2 | 0 | 4 | 0 | 1 | 0 |
| Infiltration of Renal Tubule Epithelium Cells | 0 | 0 | 5 | 0 | 0 | 1 | 3 | 1 | 0 | 1 | 2 | 1 | 0 | 3 | 2 | 0 |

Results (1) It was found that the control group which received only gentamycin showed remarkable increase in NAG and LDH values after 15 days of administration of gentamycin, as well as increase in BUN value. Thus, it was clearly recognized that kidney injury was caused by gentamycin.

(2) Isoliquiritigenin acted to remarkably suppress the increase in NAG, LDH, and BUN values almost dose-dependently as compared to the control group in which gentamycin induced kidney injury.

(3) Also, in the pathological views of the kidney tissues, the group which received 300 mg per kilogram body weight of isoliquiritigenin showed remarkable improvement with respect to the necrosis, degeneration, regeneration, division, and infiltration of the epithelium cells of the renal tubule as compared to the control group in which gentamycin induced kidney injury. In addition, the groups which received 50 and 150 mg per kilogram body weight, respectively, of isoliquiritigenin also showed improvement in the necrosis, degeneration, regeneration, and division of the epithelium cells of the renal tubule.

It is clear from the above-stated results of the tests that isoliquiritigenin remarkably improves acute nephritis induced by a drug, and it can be considered that isoliquiritigenin is very useful in treating acute nephritis caused by drugs.

Example 3

Activity of isoliquiritigenin against acute kidney injury induced by cis-platinum In this Example, tests were conducted by choosing cis-platinum which is an anti-cancer drug and is known to have a very strong effect of inducing functional disorders of the kidney as the inducer of a model drug-induced acute nephritis, a functional disorder of the kidney caused by abnormality in the metabolic functions, and by examining the action of isoliquiritigenin against the acute nephritis induced by cis-platinum, to confirm the efficacy (effects in the prevention and therapy) of the medicine in accordance with the present invention.

(1) Prevention Tests

A group of ten ddy male mice each weighing 20 to 25 g were orally administered with 200 mg per kilogram body weight per day of isoliquiritigenin suspended in 1%-CMC aqueous solutions, for 5 continuous days, subcutaneously injected with 16 mg per kilogram body weight of cis-platinum dissolved in physiological salines at a ratio of 2 mg per 10 ml, once on the fifth day, and were treated moreover for 5 continuous days orally administered with isoliquiritigenin in the same manner as above. Thereafter, blood samples were collected, and, after they were centrifuged at 300 rpm for 15 minutes, BUN in the serum was measured.

(2) Therapy Tests

A group of ten ddy male mice each weighing 20 to 25 g were subcutaneously injected with 16 mg per kilogram body weight of cis-platinum dissolved in physiological saline solution at a ratio of 2 mg/10 ml once, and with oral administration of 200 mg per kilogram body weight per day of isoliquiritigenin suspended in 1%-CMC aqueous solution, for 5 continuous days. Thereafter, blood samples were collected, and after they were centrifuged at 3000 rpm for 15 minutes, BUN in the serum was measured.

In each of the tests (1) and (2), an isoliquiritigenin only administration control group and a cis-platinum induced nephritis control group were employed and were compared with the cis-platinum and isoliquiritigenin administration group. The isoliquiritigenin only administration control group consisted of ten ddy male mice, each weighing 20 to 25 g, which were orally administered with 200 mg per kilogram body weight per day of isoliquiritigenin, for continuous days. The cis-platinum induced nephritis control group consisted of ten ddy male mice, each weighing 20 to 25 g, which were treated in exactly the same manner as that of the cis-platinum and isoliquiritigenin administration group except that the mice in this control group were subcutaneously injected with 16 mg per kilogram body weight of cis-platinum once, and orally administered with 1%-CMC aqueous solutions, in place of isoliquilirigenin, for continuous days. The results of the tests are shown in Table 3.

TABLE 3

Activity of Isoliquiritigenin Against Cis-platinum-Induced Acute Nephritis

|  | BUN (mg/dl) | |
|---|---|---|
|  | (1) Prevention Fest mean ± SD | (2) Therapy Test mean ± SD |
| Non-Treated Control Group | 18.6 ± 0.9 | 19.2 ± 0.9 |
| Isoliquiritigenin only Administration Control Group | 21.8 ± 0.6 | 19.8 ± 0.9 |
| Kidney Injury-Induced Control Group | 142.8 ± 17.2 | 128.4 ± 19.0 |
| Isoliquiritigenin Administered Kidney Injury-Induced Group | 48.9 ± 13.4 | 63.0 ± 12.4 |

Results (1) The nephritis-induced control groups which received cis-platinum showed remarkable increases in BUN values when compared with non-treated control groups. Thus, it was clearly recognized that acute kidney injury was caused by cis-platinum.

(2) Isoliquiritigenin was found to remarkably supress increases in BUN value in both the prevention tests and the therapy tests when compared with the nephritis-induced control groups.

(3) The isoliquiritigenin only administration control groups wherein no kidney injury was caused showed results which are not much different from those shown by non-treated control groups. Thus, it was clearly found that isoliquiritigenin specifically supresses increase in BUN value caused by kidney injury.

It is clear from the above-stated results of the tests that isoliquiritigenin remarkably improves acute nephritis induced by drugs. Thus, it can be considered that isoliquiritigenin is very useful in the prevention and therapy of acute kidney injury caused by drugs.

Example 4

Activity of isoliquiritigenin against rat anti-GBM (glomerular basement membrane) antibody nephritis.

It is considered that 70% of chronic kidney diseases of human beings is caused by the intermediary of the immunological mechanism. Observations suggesting the involvement of the immunological mechanism in lot of cases of glomerular nephritis have been made, particularly concerning glomerular nephritis. On the basis of these facts, various studies have been made to prepare animal test models as models of chronic nephritis of human beings. Among these models, the Masugi nephritis model, which has been developed in Japan, is a nephritis model in which nephritis is caused by the antibody against the glomerular tissue antigen (GBM), and this model is used widely in the world. Therefore, in this example, the present inventors chose the Masugi nephritis model as a model of chronic nephritis of human beings, and conducted tests according to the method reported in *NIHON JINZOH GAKUKAI SHI*, vol. 23, pages 323 to 331, 1981, and in *NIHON YAKURI GAKUKAI SHI*, vol. 77, pages 407 to 417, 1981, so as to confirm the efficacy of the medicine of the present invention.

SD strain male rats each weighing 180 to 200 g (produced by Nihon Charles River K.K., 7 rats for a nephritis-induced group and 6 rats each for the other groups) were intravenously injected with 0.5 ml per rat of rabbit serum causative of the antibody against GBM within the rats, and immediately thereafter orally administered with 5 ml per kilogram body weight of suspensions in which 30, 100, or 300 mg per kilogram body weight per day of isoliquiritigenin was suspended in 1%-CMC aqueous solutions, everyday for 3 continuous weeks. The rats in the nephritis-induced control group were intravenously injected with 0.5 ml per rat of rabbit serum causative of the antibody against GBM within the rats, and orally administered with 5 ml per kilogram body weight of 1%-CMC aqueous solutions, everyday for 3 continuous weeks. Samples of the urine of the rats were collected using metabolism cages for a period of 24 hours from the final administration day which is 3 weeks after the injection of the rabbit serum to the next day. After the amounts of the urine were measured, the urine samples were centrifuged at 3000 rpm for 15 minutes, and the supernatant liquids were examined by measuring the activities of lactate dehydrogenase (LDH), the amount of alkaline phosphatase (ALP), and the amount of protein by means of an automatic analyzer (AU-550, a product of Olympus Kohgaku Kohgyoh). After the completion of the collection of the urine samples, blood samples were collected from the aorta abdominalis while the rats were anesthetized with ether. The serum of the blood samples was centrifuged at 3000 rpm for 15 minutes and was examined by measuring BUN, creatinine, ALP, total cholesterol, total protein, and albumin. The results of the tests are shown in Table 4.

TABLE 4

Biochemical Parameters of Blood and Urine 3 Weeks after Administration of Rabbit Serum causative of Antibody against GBM

| | Biochemical Parameters of Blood | | | | | | |
|---|---|---|---|---|---|---|---|
| | BUN (mg/dl) Mean ± S.E | Creatinine (mg/dl) Mean ± S.E | ALP (IU/l) Mean ± S.E | Total Cholesterol (mg/dl) Mean ± S.E | Total Protein (g/dl) Mean ± S.E | Albumin (g/dl) Mean ± S.E | A/G Ratio Mean ± S.E |
| Non-Treated Control Group | 21.4 ± 0.65 | 0.45 ± 0.02 | 617 ± 33.4 | 76 ± 2.5 | 6.61 ± 0.11 | 3.6 ± 0.04 | 1.2 ± 0.02 |
| Nephritis-Induced Control Group | 21.5 ± 0.79 | 0.46 ± 0.02 | 390 ± 44.6 | 199 ± 58.6 | 6.72 ± 0.18 | 3.0 ± 0.19 | 0.8 ± 0.11 |
| Isoliquiritigenin 30 mg/Kg | 24.2 ± 0.90 | 0.45 ± 0.01 | 544 ± 23.3 | 126 ± 17.1 | 6.29 ± 0.03 | 3.1 ± 0.08 | 1.0 ± 0.04 |
| 100 mg/Kg | 23.1 ± 1.10 | 0.42 ± 0.01 | 598 ± 61.6 | 119 ± 7.3 | 6.29 ± 0.05 | 3.2 ± 0.08 | 1.1 ± 0.04 |
| 300 mg/Kg | 24.2 ± 0.82 | 0.42 ± 0.01 | 486 ± 41.2 | 86 ± 8.6 | 6.31 ± 0.08 | 3.4 ± 0.16 | 1.2 ± 0.04 |

| Biochemical Parameters of Urine Stored for 24 Hours | | |
|---|---|---|
| Total Protein (mg/Urine) | Total ALP (U/Urine) | Total LDH (U/Urine) |

TABLE 4-continued

Biochemical Parameters of Blood and Urine 3 Weeks after Administration of Rabbit Serum causative of Antibody against GBM

|  | Mean ± S.E | Mean ± S.E | Mean ± S.E |
|---|---|---|---|
| Non-Treated Control Group | 49.7 ± 4.3 | 3.43 ± 1.16 | 0.34 ± 0.03 |
| Nephritis-Induced Control Group | 307.0 ± 128.1 | 5.27 ± 1.13 | 1.40 ± 0.66 |
| Isoliquiritigenin 30 mg/Kg | 239.0 ± 66.1 | 4.63 ± 0.91 | 0.53 ± 0.86 |
| 100 mg/Kg | 207.7 ± 55.5 | 4.20 ± 0.45 | 0.40 ± 0.06 |
| 300 mg/Kg | 177.9 ± 41.7 | 4.03 ± 0.56 | 0.38 ± 0.08 |

Results (1) The nephritis-induced control group showed, after 3 weeks, remarkable increases in total protein, total ALP, and total LDH in the urine, when compared with a non-treated control group. Although no remarkable changes in BUN and creatinine in blood were recognized, decrease in ALP and increase in total cholesterol were observed. In addition, although no change in total protein in the serum was recognized, decrease in the albumin content was observed, and decrease in the A/G ratio accompanying this was recognized. It is clearly recognized from these results that kidney injury was caused by the intermediary of the immune system.

(2) The groups administered with isoliquiritigenin in the respective dosages showed remarkable suppression of increase in total protein, total ALP, and total LDH in the urine, when compared with the nephritis-induced control group. In addition, remarkable improvements were found in the amounts of ALP, total cholesterol, and albumin in the blood.

It can be considered from the above-mentioned results that isoliquiritigenin is very useful in the prevention and therapy of kidney injury caused by the intermediary of the immunological mechanism.

Example 5

Activity of isoliquiritigenin against liver injury induced by d-galactosamine d-Galactosamine is a compound capable of inducing injury which is similar to the lesion of viral hepatitis of human beings, and is used to induce a model of hepatitis. Therefore, in this example, the present inventors conducted tests in accordance with the method reported by Sakamoto et al in *SHINYAKU-KAIHATSU NO TAMENO YAKUKOH SCREENING HOHOH, VOL 1* (Methods of Screening Drug Effects for Developing Novel Medicines), pages 69 to 82, 1984, by Kohji Sakamoto, published by Seishi Shoin, so as to confirm the efficacy of the medicine in accordance with the present invention.

Wistar strain male rats each weighing 180 to 200 g (produced by Nihon Charles River K.K., 6 rats in each group) were orally administered with 5 ml per kilogram body weight of a mixture in which 10 or 30 mg per kilogram body weight per day of isoliquiritigenin was suspended in 1%-CMC aqueous solutions, for 5 days, and intraperitoneally injected with 250 mg per kilogram body weight of d-galactosamine dissolved in 5 ml per kilogram body weight of physiological saline solutions, one hour after the administration of isoliquiritigenin on the 4th day. 48 hours after the administration of d-galactosamine, blood samples were collected from aorta abdominalis while the rats were anesthetized with ether. The serum of the blood samples centrifuged at 3000 rpm for 15 minutes were examined by measuring glutamic-oxaloacetic transaminase (GOT), glutamic-pyruvic transaminase (GPT), and ALP by an automatic analyser (AU-550).

A liver injury-induced control group was treated in exactly the same manner as that of the isoliquiritigenin administration groups except that rats in this control group were orally administered with 1%-CMC aqueous solutions in place of the suspensions of isoliquiritigenin in 1%-CMC aqueous solutions.

Positive control groups were treated in exactly the same manner as that of the isoliquiritigenin administration groups except that rats in two positive control groups were orally administered with 30 or 100 mg per kilogram body weight per day of malotilate, in place of isoliquiritigenin, suspended in 1%-CMC aqueous solutions, while rats in the other two positive control groups were orally administered with 30 or 100 mg per kilogram body weight per day of cianidanol, in place of isoliquiritigenin, suspended in similar aqueous solutions. The results of the tests are shown in Table 5.

TABLE 5

Biochemical Parameters of Blood 48 Hours After Administration of d-Galactosamine

|  |  | GOT (IU/l) mean ± SD | GPT (IU/l) mean ± SD | ALP (IU/l) mean ± SD |
|---|---|---|---|---|
| Non-Treated Control Group |  | 71 ± 8 | 31 ± 3 | 587 ± 62 |
| Liver Injury-Induced Control Group |  | 120 ± 29 | 46 ± 14 | 699 ± 140 |
| Isoliquiritigenin | 10 mg/Kg | 100 ± 23 | 36 ± 6 | 629 ± 139 |
| Isoliquiritigenin | 30 mg/Kg | 76 ± 17 | 30 ± 4 | 771 ± 203 |
| Malotilate | 30 mg/Kg | 141 ± 29 | 51 ± 5 | 801 ± 190 |
| Malotilate | 100 mg/Kg | 110 ± 27 | 40 ± 12 | 770 ± 179 |
| Cianidanol | 30 mg/Kg | 96 ± 17 | 43 ± 9 | 829 ± 123 |
| Cianidanol | 100 mg/Kg | 90 ± 14 | 40 ± 17 | 670 ± 127 |

Results (1) The liver injury-induced control group showed obvious increase in GOT, GPT, and ALP when compared with a non-treated control group.

(2) The isoliquiritigenin administration group of rats which received 10 mg per kilogram body weight of isoliquiritigenin showed suppression of increase in GOT, GPT, and ALP, when compared with the liver-injury induced control group, and the isoliquiritigenin administration group of rats which received 30 mg per kilogram body weight of isoliquiritigenin showed remarkable improvement in GOT and GPT values.

(3) The positive control groups which received 100 mg per kilogram body weight of malotilate or cianidanol showed substantially the same levels of suppression of increase in GOT and GPT values as those showed by the isoliquiritigenin administration group which received 10 mg per kilogram body weight of isoliquiritigenin.

It is clearly recognized from the above-mentioned results that isoliquiritigenin suppresses d-galactosamine-induced injury to the liver in dosages smaller than those of malotilate and cianidanol. Thus, it can be considered that isoliquiritigenin is useful in the prevention and therapy of liver injury such as viral hepatitis.

Examples 6 and 7

It is considered that carbon tetrachloride generates free radicals with a very high reactivity by the action of drug metabolizing enzyme systems in liver cells, and these free radicals may strongly depress the cell activity by combining with protein of the liver cell membranes or may cause peroxidation of membrane lipids of the organelles, thus leading to necrosis of liver cells and accumulation of liver fats. Accordingly, carbon tetrachloride is widely used to induce test models of acute drug-induced hepatitis of human beings, fatty liver, chronic hepatitis, and liver cirrhosis.

Therefore, in these examples 6 and 7, the present inventors conducted tests in accordance with a method reported in *JAPAN JOURNAL OF PHARMACOLOGY*, vol. 31, pages 15 to 21, 1981, by Imaizumi et al, and a method reported in *NIHON YAKURIGAKUKAI SHI*, vol. 80, pages 83 to 91, 1982, by Minoru Katoh et al, to confirm the efficacy of the medicine in accordance with the present invention.

Example 6

Activity of isoliquiritigenin against acute liver injury induced by carbon tetrachloride (CCl4)

Wistar strain male rats each weighing 180 to 200 g (produced by Nihon Charles river K.K., 6 rats in each group) orally administered with 10 or 30 mg per kilogram body weight per day of isoliquiritigenin suspended in 1%-CMC aqueous solutions, for 4 continuous days. Rats in a solution control group were orally administered with 5 ml per kilogram body weight per day of 1%-CMC aqueous solutions, for 4 continuous days. Two positive control groups were orally administered with 30 or 100 mg per kilogram body weight per day of malotilate suspended in 1%-CMC aqueous solutions, for 4 continuous days, and other two positive control groups were orally administered with 30 or 100 mg per kilogram body weight per day of cianidanol suspended in 1%-CMC aqueous solutions, for 4 continuous days.

The rats were subcutaneously injected with 0.2 ml per kilogram body weight per day of carbon tetrachloride, which was a reagent for precision analysis, everyday for three consecutive days from the second day of the isoliquiritigenin administration.

24 hours after the last administration of carbon tetrachloride, blood samples were collected from aorta abdominalis while the rats were anesthetized with ether. The blood samples were centrifuged at 3000 rpm for 15 minutes and the serum was examined by measuring GOT and GPT values using an automatic analyser (AU-550, a product of Olympus Kohgaku Kohgyoh). The results of the tests are shown in Table 6.

TABLE 6
Biochemical Parameters of Blood 24 Hours After Last Administration of Carbon Tetrachloride

|  |  | GOT (IU/l) mean ± SD | GPT (IU/l) mean ± SD |
|---|---|---|---|
| Non-Treated Control group |  | 71 ± 8 | 31 ± 3 |
| Liver Injury-Induced Control Group |  | 202 ± 120 | 74 ± 38 |
| Isoliquiritigenin | 10 mg/Kg | 134 ± 33 | 60 ± 21 |
| Isoliquiritigenin | 30 mg/Kg | 104 ± 15 | 36 ± 3 |
| Malotilate | 30 mg/Kg | 153 ± 36 | 69 ± 9 |
| Malotilate | 100 mg/Kg | 140 ± 24 | 59 ± 21 |
| Cianidanol | 30 mg/Kg | 154 ± 43 | 85 ± 55 |
| Cianidanol | 100 mg/Kg | 175 ± 45 | 89 ± 49 |

Results (1) It was found that the liver injury-induced control group showed remarkable increases in GOT and GPT values when compared with a non-treated control group. Thus, it was clearly recognized that liver injury was caused by carbon tetrachloride.

(2) Each of the isoliquiritigenin administration groups with the respective amounts used showed remarkable improvement in GOT and GPT values when compared to the liver injury-induced control group.

(3) Each of the positive control groups which received 30 or 100 mg per kilogram body weight of malotilate or cianidanol showed suppression of increase in GOT and GPT values to substantially the same extent as that showed by the isoliquiritigenin administration group which received 10 mg per kilogram body weight of isoliquiritigenin.

It can be considered from the above-mentioned results that isoliquiritigenin suppresses liver injury induced by carbon tetrachloride in smaller amounts than those of malotilate and cinanidanol, and is thus useful in the prevention and therapy of acute liver injury.

Example 7

Activity of isoliquiritigenin against chronic liver injury induced by carbon tetrachloride Wistar strain male rats each weighing 180 to 200 g (produced by Nihon Charles river K.K., 6 rats in each group) were orally administered with 30 mg per kilogram body weight per day of isoliquiritigenin suspended in 1%-CMC aqueous solutions, everyday for 3 continuous weeks. Rats in a solution control group were orally administered with 5 ml per kilogram body weight per day of 1%-CMC aqueous solutions, every day for 3 continuous weeks. Rats in a positive control group were orally administered with 30 mg per kilogram body weight per day of malotilate suspended in 1%-CMC aqueous solutions everyday for 3 continuous weeks, and rats in another positive control groups were orally administered with 30 mg per kilogram body weight per day of cianidanol suspended in 1%-CMC aqueous solutions, everyday for 3 continuous weeks.

The rats were intraperitoneally injected with 0.5 ml per kilogram body weight per day of carbon tetrachloride, for three consecutive weeks from the third day of the isoliquiritigenin administration twice a week.

On the 4th day after the last administration of carbon tetrachloride, blood samples were collected from aorta abdominalis while the rats were anesthetized with ether. The blood samples were centrifuged at 3000 rpm for 15 minutes and the serum was examined by measuring GOT and GPT values using an automatic analyser (AU-550, a product of Olympus Kohgaku Kohgyoh). The results of the tests are shown in Table 7.

TABLE 7

Biochemical Parameters of Blood 3 Weeks after Induction of Chronic Liver Injury by Carbon Tetrachloride

|  |  | GOT (IU/l) mean ± SD | GPT (IU/l) mean ± SD |
|---|---|---|---|
| Non-Treated Control group |  | 71 ± 8 | 31 ± 3 |
| Liver Injury-Induced Control Group |  | 509 ± 106 | 212 ± 65 |
| Isoliquiritigenin | 30 mg/Kg | 404 ± 73 | 183 ± 63 |
| Malotilate | 30 mg/Kg | 202 ± 17 | 41 ± 4 |
| Cianidanol | 30 mg/Kg | 416 ± 131 | 183 ± 107 |

Results (1) The liver injury-induced control group showed remarkable increase in GOT and GPT when compared with the non-treated control group. Thus, it was clearly recognized that serious injury to the liver was caused by carbon tetrachloride.

(2) The isoliquiritigenin administration group showed substantially the same level of suppression of increase in GOT and GPT as that showed by the positive control group which received cianidanol. The positive control group which received malotilate showed remarkable suppression in this series of tests.

It can be considered from the above-mentioned results of the tests that isoliquiritigenin is useful in the prevention and therapy of chronic liver injury.

Example 8

Activity of isoliquiritigenin against acute liver injury induced by cis-platinum It is known that cis-platinum, a carcinostatic drug, causes injury to the liver as well as to the kidney (CANCER TREATMENT REPORTS, vol. 62, No. 12, pages 2125 to 2126, 1978, by F. Cawalli et al). The present inventors have found that the carcinostatic drug cis-platinum causes injury to the liver besides it causes injury to the kidney and that it causes liver injury in a lower dosage than that in which it causes kidney injury. In this example, the activity of isoliquiritigenin against acute liver injury induced by cis-platinum was examined, to confirm the efficacy of the medicine of the present invention.

A group consisting of six Wistar strain male rats (produced by Nihon Charles River K.K.), each weighing 150 to 180 g, were subcutaneously injected with 8.5 mg per kilogram body weight of cis-platinum dissolved in physiological saline solution at a ratio of 2 mg per 10 ml once, and orally administered with 200 mg per kilogram body weight per day of isoliquiritigenin suspended in 1%-CMC aqueous solutions, for 10 continuous days.

The rats were then dissected, and liver samples dyed with hematoxylin-eosin were prepared and observed under a microscope.

A liver injury-induced control group consisted of six Wistar strain male rats (produced by Nihon Charles River K.K.), each weighing 150 to 180 g, were treated in exactly the same manner as that of the isoliquiritigenin administration group except that the rats in this control group were orally administered with 1%-CMC aqueous solutions alone, in place of isoliquiritigenin, for 10 continuous days. The results of the tests are shown in Table 8.

TABLE 8

Pathological Views of Isoliquiritigenin against Acute Liver Injury Induced by Cis-platinum

| Group (n = 6) | Pathological views of Liver Injury Degeneration Grade | | |
|---|---|---|---|
|  | − | + | ++ |
| Liver Injury-Induced Control Group | 0 | 3 | 3 |
| Isoliquiritigenin 200 mg/Kg | 3 | 3 | 0 |
| Non-Treated Control Group | 6 | 0 | 0 |

Results (1) It was clearly recognized that the liver injury-induced control group which received cis-platinum caused injury to the livers when compared with the non-treated control group.

(2) Isoliquiritigenin remarkably suppressed injury to the livers induced by cis-platinum.

It is clear from the above-mentioned results that isoliquiritigenin remarkably improves cis-platinum-induced acute liver injury. Thus, it can be considered that isoliquiritigenin is very useful in therapy of acute liver injury induced by drugs.

Example 9

Activity of isoliquiritigenin against acute kidney and liver injuries induced by cis-platinum As described above, it has become clear that isoliquiritigenin is useful in the prevention and therapy of both kidney injury and liver injury. Therefore, in this example, the present inventors conducted the following prevention tests and therapy tests using the same test models as used in examples 3 and 8 wherein kidney or liver injury was caused by cis-platinum, a carcinostatic drug, to confirm the efficacy of the medicine in accordance with the present invention against a complication resulting from kidney and liver injuries.

(1) Prevention Tests

Fihser strain male rat (produced by Nihon Charles River K.K., 3 rats in each groups), each weighing 215 to 240 g, were either orally administered or intraperitoneally injected with 20 mg per kilogram body weight per day of isoliquiritigenin suspended in 1%-CMC aqueous solutions once a day, for 12 continuous days. From the 6th day after the start of the isoliquiritigenin administration, the rats in these groups subcutaneously injected with 2 mg per kilogram body weight per day of cis-platinum dissolved in physiological saline solution at a ratio of 2mg per 10 ml, once a day for 4 continuous days. Similar isoliquiritigenin administration was effected during the cis-platinum injection days immediately after the injection of cis-platinum, and during 3 days following the completion of the cis-platinum administration.

Rats in a kidney and liver injury-induced control group were injected with cis-platinum in the same manner as that of the isoliquiritigenin administration groups, and were treated in the same manner as that of these groups except that rats in this control group were orally administered with 1%-CMC aqueous solutions, in place of isoliquiritigenin suspended in 1%-CMC aqueous solutions.

24 hours after the completion of the administration of isoliquiritigenin, blood samples were collected from the aorta abdominalis while the rats were anesthetized with ether, and autopsy was performed. After the livers were removed, liver samples were fixed in 10%-buffer formalin, dyed with hematoxylin-eosin and with PAS, and observed under a microscope. The collected blood was centrifuged at 3000 rpm for 15 minutes, and the serum was examined by measuring BUN using an automatic analyser (AU-550, a product of Olympus Kohgaku Kohgyoh).

(2) Therapy Tests

Fisher strain male rats (produced by Nihon Charles River K.K., 3 rats in each group), each weighing 215 to 240 g, were first divided into two groups. Rats in these groups were subcutaneously injected with 2mg per kilogram body weight per day of cis-platinum dissolved in physiological saline solution at a ratio of 2 mg per 10 ml, once a day for 4 days, thereby inducing kidney and liver injuries. Everyday, immediately after the injection of cis-platinum, the rats in the two groups were either orally administered or intraperitoneally injected with 20 mg per kilogram body weight per day of isoliquiritigenin suspended in 1%-CMC aqueous solutions, once a day for 4 continuous days, and the rats were also administered with isoliquiritigenin once a day for 3 continuous days after the last injection of cis-platinum. The rats in a kidney and liver injury-induced control group were injected with cis-platinum in the same manner as those of the isoliquiritigenin administration groups, and were treated in the same manner as the rats of these groups except that rats in this control group were orally administered with 1%-CMC aqueous solutions, in place of isoliquiritigenin suspended in 1%-CMC aqueous solutions.

24 hours after the completion of the administration of isoliquiritigenin, blood samples were collected from the aorta abdominalis wile the rats were anesthetized with ether, and autopsy was performed. After the livers were removed, liver samples were fixed in 10%-buffer formalin, dyed with hematoxylin-eosin and with PAS, and observed through a microscope. The collected blood was centrifuged at 3000 rpm for 15 minutes, and the serum was examined by measuring BUN using an automatic analyser (AU-550, a product of Olympus Kohgaku Kohgyoh).

A non-treated control group consisted of Fisher strain male rats (produced by Nihon Charles River K.K., 3 rats in each group), each weighing 215 to 240 g, which were orally administered with 1%-CMC aqueous solutions, in place of isoliquiritigenin suspended in 1%-CMC aqueous solution, once a day for 12 days. 24 hours after the completion of the administration, blood samples were collected, and autopsy was performed. Also, measurement of BUN and observation of liver samples were performed in similar manners as those described above. The results of the tests are shown in Tables 9 and 10.

TABLE 9

Urea Nitrogen in Blood Samples after 4 Days of Cis-platinum Administration

| | BUN (mg/dl) | |
|---|---|---|
| | (1) Prevention Test mean ± SD | (2) Therapy Test mean ± SD |
| Non-Treated Control Group | 23 ± 3 | 23 ± 3 |
| Kidney and Liver Injury-Induced Control Group | 84 ± 27 | 66 ± 13 |
| Isoliquiritigenin (Oral Administration) 20 mg/Kg | 51 ± 18 | 47 ± 16 |
| Isoliquiritigenin (Intraperitoneal Injection) | 41 ± 1 | 38 ± 2 |

TABLE 10

Pathological Views of Liver Injury after 4 days of Cis-platinum Administration

| | | Pathological Views of Liver-Injury Degeneration Grade | | |
|---|---|---|---|---|
| Group (n = 3) | | − | + | ++ |
| (1) Prevention Test | | | | |
| Kidney and Liver Injury-Induced Control Group | | 1 | 2 | 0 |
| Isoliquiritigenin (Oral Administration) | 20 mg/Kg | 2 | 1 | 0 |
| Isoliquiritigenin (Intraperitoneal Injection) | 20 mg/Kg | 2 | 1 | 0 |
| (2) Therapy Test | | | | |
| Kidney and Liver Injury-Induced Control Group | | 1 | 2 | 0 |
| Isoliquiritigenin (Oral Administration) | 20 mg/Kg | 2 | 1 | 0 |
| Isoliquiritigenin (Intraperitoneal Injection) | 20 mg/Kg | 3 | 0 | 0 |
| Non-Treated Control Group | | 3 | 0 | 0 |

Results (1) It was clearly recognized from the fact that the kidney and liver injury-induced groups showed increase in BUN and from the pathological views of liver tissues and cells, i.e., from the views of oxyphilic degeneration and vacuolar degeneration of the liver cells, that injury to the kidney and the liver was caused by cis-platinum when compared with the non-treated groups.

(2) In both the prevention tests and the therapy tests, the isoliquiritigenin administration groups, which received isoliquiritigenin either orally or by intraperitoneal injection, showed remarkable suppression of increase in BUN, and suppression of development of liver injury was also recognized when compared with the kidney and liver injury-induced groups.

It can be considered from the above-mentioned results and from the results of examples 3 and 8 that isoliquiritigenin is very useful in the prevention and therapy for complications resulting from kidney and liver injuries.

The foregoing examples show the efficacy of the medicine in accordance with the present invention in treating individual kidney and liver diseases and complications thereof.

The following examples give examples of prescription in which the formulation and the components of the medicine are specified.

It is to be understood that the present invention are not limited by the following examples.

Example 10

Examples of prescription of tablets each containing 5 or 25 mg of the active ingredient are as given below:

Prescription Example 1 (5 mg tablet)

| | |
|---|---|
| isoliquiritigenin | 5 |
| lactose | 137 |
| starch | 45 |
| calcium carboxylmethyl cellulose | 10 |
| talc | 2 |
| magnesium stearate | 1 |
| | 200 mg per tablet |

Prescription Example 2 (25 mg tablet)

| | |
|---|---|
| isoliquiritigenin | 25 |
| lactose | 120 |
| starch | 42 |
| calcium carboxylmethyl cellulose | 10 |
| talc | 2 |
| magnesium stearate | 1 |
| | 200 mg per tablet |

Details of the manufacturing method is as given below.

Crystals of isoliquiritigenin were ground, lactose and starch were added thereto, and they were mixed. 10% of starch paste was added to the mixture, and they were agitated, thereby obtaining a granule. After the granule was dried, the grains were dressed to a grain size of about 850 microns. It was then mixed with talc and magnesium stearate, and the mixture was formulated into tablets.

Example 11

Prescription Example (20 mg capsule)

| | |
|---|---|
| isoliquiritigenin | 20 |
| lactose | 53 |
| starch | 25 |
| magnesium stearate | 2 |
| | 100 mg per capsule |

Isoliquiritigenin was well ground, and starch, lactose, and magnesium stearate were added thereto. After they had been mixed adequately, the mixture were charged into a capsule.

As described above, the present invention provides a medicine for use in the therapy and prevention of kidney and liver diseases characterized by containing as the active ingredient isoliquiritigenin or a pharmaceutically acceptable salt thereof. According to the present invention, there is provided a medicine for use in the therapy and prevention of kidney and liver diseases which exhibits excellent therapeutic and preventive effects with respect to a wide range of kidney or liver diseases individually developed or to complications resulting from diseases of these organs.

INDUSTRIAL APPLICATION

The medicine in accordance with the present invention which contains isoliquiritigenin as the active ingredient has a broad scope of applications such as a medicine for use in the therapy and prevention of kidney diseases, a medicine for use in the therapy and prevention of liver diseases, and a medicine for use in the therapy and prevention of complications resulting from kidney and liver diseases. Therefore, the medicine in accordance with the present invention exhibits excellent therapeutic and preventive effects with respect to a wide range of kidney or liver diseases individually developed or to complications resulting from diseases of these organs.

We claim:

1. A method for the therapy and prevention of kidney diseases or liver diseases, comprising administering to a mammal a medicine containing a therapeutically or prophylactically effective amount for the therapy and prevention of kidney diseases, or liver diseases of isoliquiritigenin as an active ingredient.

2. The method according to claim 1, wherein said medicine contains 0.1 to 100% by weight of isoliquiritigenin.

3. The method according to claim 2, wherein said medicine is in the form of a formulation selected from the group consisting of a tablet, a capsule, a granule, a powder, a fine granule, a pill, a troche, a buccal, a suppository, an ointment, an injection, an emulsion, a suspension and a syrup.

4. The method according to claim 3, wherein said medicine further contains at least one additive selected from the group consisting of an excipient, a binder, a disintegrator, a lubricant, a preservative, an antioxidant, an isotonizing agent, a buffer, a coating agent, a corrigent, a solution adjuvant, a base, a dispersing agent, a stabilizer and a colorant.

5. The method according to claim 1, wherein said diseases are kidney diseases.

6. The method according to claim 5, wherein said medicine contains 0.1 to 100% by weight of isoliquiritigenin.

7. The method according to claim 6, wherein said medicine is in the form of a formulation selected from the group consisting of a tablet, a capsule, a granule, a powder, a fine granule, a pill, a troche, a buccal, a suppository, an ointment, an injection, an emulsion, a suspension and a syrup.

8. The method according to claim 7, wherein said medicine further contains at least one additive selected from the group consisting of an excipient, a binder, a disintegrator, a lubricant, a preservative, an antioxidant, an isotonizing agent, a buffer, a coating agent, a corrigent, a solution adjuvant, a base, a dispersing agent, a stabilizer and a colorant.

9. The method according to claim 5, wherein said kidney diseases are at least one of acute nephritis caused by a functional disorder of a kidney due to an abnormality in metabolic function, and chronic nephritis developed from said acute nephritis.

10. The method according to claim 9, wherein said medicine contains 0.1 to 100% by weight of isoliquiritigenin.

11. The method according to claim 10, wherein said medicine is in the form of a formulation selected from the group consisting of a tablet, a capsule, a granule, a powder, a fine granule, a pill, a troche, a buccal, a suppository, an ointment, an injection, an emulsion, a suspension and a syrup.

12. The method according to claim 11, wherein said medicine further contains at least one additive selected from the group consisting of an excipient, a binder, a disintegrator, a lubricant, a preservative, an antioxidant, an isotonizing agent, a buffer, a coating agent, a corrigent, a solution adjuvant, a base, a dispersing agent, a stabilizer and a colorant.

13. The method according to claim 9, wherein said abnormality in metabolic function is caused by a drug.

14. The method according to claim 13, wherein said medicine contains 0.1 to 100% by weight of isoliquiritigenin.

15. The method according to claim 14, wherein said medicine is in the form of a formulation selected from the group consisting of a tablet, a capsule, a granule, a powder, a fine granule, a pill, a troche, a buccal, a suppository, an ointment, an injection, an emulsion, a suspension and a syrup.

16. The method according to claim 15, wherein said medicine further contains at least one additive selected from the group consisting of an excipient, a binder, a disintegrator, a lubricant, a preservative, an antioxidant, an isotonizing agent, a buffer, a coating agent, a corrigent, a solution adjuvant, a base, a dispersing agent, a stabilizer and a colorant.

17. The method according to claim 5, wherein said kidney diseases are at least one of a group of functional disorders of the kidney consisting of acute nephritis caused by the intermediary of the immunological mechanism, and chronic nephritis developed from said acute nephritis.

18. The method according to claim 17, wherein said medicine contains 0.1 to 100% by weight of isoliquiritigenin.

19. The method according to claim 18, wherein said medicine is in the form of a formulation selected from the group consisting of a tablet, a capsule, a granule, a powder, a fine granule, a pill, a troche, a buccal, a suppository, an ointment, an injection, an emulsion, a suspension and a syrup.

20. The method according to claim 19, wherein said medicine further contains at least one additive selected from the group consisting of an excipient, a binder, a disintegrator, a lubricant, a preservative, an antioxidant, an isotonizing agent, a buffer, a coating agent, a corrigent, a solution adjuvant, a base, a dispersing agent, a stabilizer and a colorant.

21. The method according to claim 5, wherein said kidney diseases are at least one of a group of functional disorders of the kidney consisting of acute nephritis caused by bacteria and virus infection, and chronic nephritis developed from said acute nephritis.

22. The method according to claim 21, wherein said medicine contains 0.1 to 100% by weight of isoliquiritigenin.

23. The method according to claim 22, wherein said medicine is in the form of a formulation selected from the group consisting of a tablet, a capsule, a granule, a powder, a fine granule, a pill, a troche, a buccal, a suppository, an ointment, an injection, an emulsion, a suspension and a syrup.

24. The method according to claim 23, wherein said medicine further contains at least one additive selected from the group consisting of an excipient, a binder, a disintegrator, a lubricant, a preservative, an antioxidant, an isotonizing agent, a buffer, a coating agent, a corrigent, a solution adjuvant, a base, a dispersing agent, a stabilizer and a colorant.

25. The method according to claim 1, wherein said kidney diseases are functional disorders of at least one kidney portion such as the glomerulus, the renal tubule, or the lupus.

26. The method according to claim 25, wherein said medicine contains 0.1 to 100% by weight of isoliquiritigenin.

27. The method according to claim 26, wherein said medicine is in the form of a formulation selected from the group consisting of a tablet, a capsule, a granule, a powder, a fine granule, a pill, a troche, a buccal, a suppository, an ointment, an injection, an emulsion, a suspension and a syrup.

28. The method according to claim 27, wherein said medicine further contains at least one additive selected from the group consisting of an excipient, a binder, a disintegrator, a lubricant, a preservative, an antioxidant, an isotonizing agent, a buffer, a coating agent, a corrigent, a solution adjuvant, a base, a dispersing agent, a stabilizer and a colorant.

29. The method according to claim 1, wherein said diseases are liver diseases.

30. The method according to claim 29, wherein said medicine contains 0.1 to 100% by weight of isoliquiritigenin.

31. The method according to claim 30, wherein said medicine is in the form of a formulation selected from the group consisting of a tablet, a capsule, a granule, a powder, a fine granule, a pill, a troche, a buccal, a suppository, an ointment, an injection, an emulsion, a suspension and a syrup.

32. The method according to claim 31, wherein said medicine further contains at least one additive selected from the group consisting of an excipient, a binder, a disintegrator, a lubricant, a preservative, an antioxidant, an isotonizing agent, a buffer, a coating agent, a corrigent, a solution adjuvant, a base, a dispersing agent, a stabilizer and a colorant.

33. The method according to claim 29, wherein said liver diseases are functional disorders of the liver caused by an abnormality in metabolic function and in biosynthetic function.

34. The method according to claim 33, wherein said medicine contains 0.1 to 100% by weight of isoliquiritigenin.

35. The method according to claim 34, wherein said medicine is in the form of a formulation selected from the group consisting of a tablet, a capsule, a granule, a powder, a fine granule, a pill, a troche, a buccal, a suppository, an ointment, an injection, an emulsion, a suspension and a syrup.

36. The method according to claim 35, wherein said medicine further contains at least one additive selected from the group consisting of an excipient, a binder, a disintegrator, a lubricant, a preservative, an antioxidant, an isotonizing agent, a buffer, a coating agent, a corrigent, a solution adjuvant, a base, a dispersing agent, a stabilizer and a colorant.

37. The method according to claim 33, wherein said abnormality in the metabolic function and in the biosynthetic function is caused by a drug.

38. The method according to claim 37, wherein said medicine contains 0.1 to 100% by weight of isoliquiritigenin.

39. The method according to claim 38, wherein said medicine is in the form of a formulation selected from the group consisting of a tablet, a capsule, a granule, a powder, a fine granule, a pill, a troche, a buccal, a suppository, an ointment, an injection, an emulsion, a suspension and a syrup.

40. The method according to claim 39, wherein said medicine further contains at least one additive selected from the group consisting of an excipient, a binder, a disintegrator, a lubricant, a preservative, an antioxidant, an isotonizing agent, a buffer, a coating agent, a corrigent, a solution adjuvant, a base, a dispersing agent, a stabilizer and a colorant.

41. The method according to claim 29, wherein said liver diseases are fatty liver or chronic hepatitis developed from fatty liver.

42. The method according to claim 41, wherein said medicine contains 0.1 to 100% by weight of isoliquiritigenin.

43. The method according to claim 42, wherein said medicine is in the form of a formulation selected from the group consisting of a tablet, a capsule, a granule, a powder, a fine granule, a pill, a troche, a buccal, a suppository, an ointment, an injection, an emulsion, a suspension and a syrup.

44. The method according to claim 43, wherein said medicine further contains at least one additive selected from the group consisting of an excipient, a binder, a disintegrator, a lubricant, a preservative, an antioxidant, an isotonizing agent, a buffer, a coating agent, a corrigent, a solution adjuvant, a base, a dispersing agent, a stabilizer and a colorant.

45. The method according to claim 29, wherein said liver diseases are viral hepatitis caused by virus infection or chronic hepatitis developed from such hepatitis.

46. The method according to claim 45, wherein said medicine contains 0.1 to 100% by weight of isoliquiritigenin.

47. The method according to claim 46, wherein said medicine is in the form of a formulation selected from the group consisting of a tablet, a capsule, a granule, a powder, a fine granule, a pill, a troche, a buccal, a suppository, an ointment, an injection, an emulsion, a suspension and a syrup.

48. The method according to claim 47, wherein said medicine further contains at least one additive selected from the group consisting of an excipient, a binder, a disintegrator, a lubricant, a preservative, an antioxidant, an isotonizing agent, a buffer, a coating agent, a corrigent, a solution adjuvant, a base, a dispersing agent, a stabilizer and a colorant.

49. The method according to claim 1, wherein said diseases are complicated diseases of the kidney and the liver.

50. The method according to claim 49, wherein said medicine contains 0.1 to 100% by weight of isoliquiritigenin.

51. The method according to claim 50, wherein said medicine is in the form of a formulation selected from the group consisting of a tablet, a capsule, a granule, a powder, a fine granule, a pill, a troche, a buccal, a suppository, an ointment, an injection, an emulsion, a suspension and a syrup.

52. The method according to claim 51, wherein said medicine further contains at least one additive selected from the group consisting of an excipient, a binder, a disintegrator, a lubricant, a preservative, an antioxidant, an isotonizing agent, a buffer, a coating agent, a corrigent, a solution adjuvant, a base, a dispersing agent, a stabilizer and a colorant.

* * * * *

UNITED STATES PATENT AND TRADEMARK OFFICE
CERTIFICATE OF CORRECTION

PATENT NO. : 4,898,890
DATED : Feb. 6, 1990
INVENTOR(S) : Toshio Satoh, et al

It is certified that error appears in the above-identified patent and that said Letters Patent is hereby corrected as shown below:

On the title page:

The first inventor's name is incorrectly spelled, Toshio Sato should read as follows:

--Toshio Satoh--

Signed and Sealed this

Thirteenth Day of August, 1991

*Attest:*

HARRY F. MANBECK, JR.

*Attesting Officer*    *Commissioner of Patents and Trademarks*